United States Patent [19]
Eek-Vancells

[11] Patent Number: 5,877,356
[45] Date of Patent: Mar. 2, 1999

[54] PROCESS FOR THE CONTINUOUS PREPARATION OF AQUEOUS FORMALDEHYDE SOLUTIONS

[75] Inventor: Lluis Eek-Vancells, Barcelona, Spain

[73] Assignee: Patentes Y Novedades, S.L., Barcelona, Spain

[21] Appl. No.: 898,126

[22] Filed: Jul. 22, 1997

Related U.S. Application Data

[63] Continuation of Ser. No. 562,813, Nov. 27, 1995, abandoned.

[30] Foreign Application Priority Data

May 16, 1995 [ES] Spain ..................................... 9500924

[51] Int. Cl.[6] ................................................... C07C 45/29
[52] U.S. Cl. ......................... 568/472; 568/473; 261/149; 261/150; 261/151; 261/161
[58] Field of Search .................................... 568/472, 473; 261/149, 150, 151, 161

[56] References Cited

U.S. PATENT DOCUMENTS 4,594,457  6/1986  Yoshikawa et al. .................... 568/473

FOREIGN PATENT DOCUMENTS

| 0100809 A1 | 2/1984 | European Pat. Off. . |
| 2218313 | 2/1974 | France . |
| 382436 0 A1 | 1/1990 | Germany . |

*Primary Examiner*—Porfirio Nazario-Gonzalez
*Assistant Examiner*—Jean F. Vollano
*Attorney, Agent, or Firm*—Staas & Halsey

[57] ABSTRACT

The process uses a supply column and additional heat exchangers associated with absorption columns. Air and methanol from outside and a subcurrent of methanol, originating from a cold methanol current exiting from the supply column, are fed to the supply column. This exiting current recirculates through the additional heat exchangers and is divided into the subcurrent which returns to the supply column and another subcurrent which is fed to an evaporator. A methanol-air mixture exits from the head of the supply column and is fed to an evaporator. The cold methanol is cooled in the supply column by evaporation of the methanol forming part of the methanol-air mixture.

18 Claims, 2 Drawing Sheets

PROCESS FOR THE CONTINUOUS PREPARATION OF AQUEOUS FORMALDEHYDE SOLUTIONS

This application is a continuation of application Ser. No. 08/562,813, filed Nov. 27, 1995, now abandoned.

DESCRIPTION

1. Field of the Invention

The invention relates to a process for the continuous preparation of aqueous formaldehyde solutions, particularly solutions having a concentration ranging from 53 wt % to 57 wt %.

2. Description of the Related Art

Commercial solutions of formaldehyde in water are conventionally prepared by the process described below.

In a reaction vessel, known as an evaporator, air is caused to flow through the methanol or methanol-water mixtures at such a set temperature that the resulting gaseous methanol-air or methanol-water-air mixture is outside the explosion limits. This gaseous mixture is caused to flow through a catalyst, silver if the dehydrogenation-oxidation process with excess methanol is selected, or metal oxides if the oxidation process with excess air is selected. In both cases, the gases flowing from the catalyst must be absorbed in water, whereby the aqueous formaldehyde solution is obtained. The process has variations according to the catalyst used.

The present invention relates to the process using silver as a catalyst and, therefore, this description is restricted only to this process.

The gases flowing through the silver catalyst contain an excess of methanol and, therefore, in the water absorption step, this methanol remains in the resulting aqueous formaldehyde solution. Although the presence of methanol may be of interest in an odd application, in the majority of cases this is not so and it must be removed from the solution. This is done in a separate distillation column, which may operate at atmospheric or at reduced pressure. The methanol collected as distillate is recirculated to the evaporator as starting methanol.

Furthermore, the methanol, formaldehyde and water which condense and are dissolved in the water are accompanied at the exit from the catalyst by non-condensable gases, the nitrogen from the air, the hydrogen formed in the reaction and small amounts of carbon dioxide, carbon monoxide, methane and unconsumed oxygen.

These non-condensable gases, insoluble in the resultant aqueous solution, entrain variable amounts of methanol, formaldehyde and water depending on the temperature of the absorption solution and on the number of steps. There are generally two or three absorption steps with recirculation of the solution in each of them independently. Since the gases arrive hot and heat is given off in the absorption process, appropriate cooling means must be available. The operating temperature in each step is important since, on the one hand, the formaldehyde dissolves better at a relative elevated temperature (60°–70° C.) while, on the other hand, the methanol is retained better at low temperatures. Where formaldehyde is concerned, the methylene glycol formation reaction according to the equation:

$$CH_2O + H_2O \leftrightarrow HOCH_2OH$$

and the polymerization reaction:

$$HOCH_2OH + CH_2O \leftrightarrow HO(CH_2O)_2H$$

$$HO(CH_2O)_2H + CH_2O \leftrightarrow HO(CH_2O)_3H$$

must be taken into account.

The polymerization reactions take place at high concentrations of formaldehyde and not very elevated temperatures, whereas at elevated temperatures (>70° C.), the depolymerization reactions may prevail.

Furthermore, the extension of the polymerization reactions is low in dilute solutions and at elevated temperatures the balance of the methylene glycol formation reaction drifts to the left, with the consequent release of formaldehyde.

The complexity of these reactions depends on the temperature and on the formaldehyde concentration.

Also, the passage of a gas through the formaldehyde solution, albeit dilute, displaces the balance to the left by removal of the formaldehyde monomer with the gas. (Walker J. F.: Formaldehyde, 3rd Ed. Reinhold Pub. Corp. 1964, page 113). The table appearing in this reference shows the great influence of the temperature on the formaldehyde values in the air, as well as the effect of the formaldehyde concentration in the solution.

The methanol, in turn, has a much higher vapour pressure and therefore an appreciable amount is lost, unless it is trapped.

In principle, whatever the absorption process used, practically all the patents cited in the literature add, at one point or the other of the plant, a water scrubbing of the gases from the absorption. (Examples: U.S. Pat. Nos. 3,113,972, 3,174,911, 4,990,685, FR 1 500 550, DE 2 444 586, EP 0 100 809). This involves a dilution of the formaldehyde solution overall.

U.S. Pat. No. 4,594,457 describes the preparation of aqueous formaldehyde solutions up to 60% with low methanol content, from mixtures of methanol, air and water vapour. In this process, an aqueous current drawn from the head of the absorption column and containing a certain amount of methanol and formaldehyde is recirculated to the catalyst which is at a temperature of up to 680° C., normally 620°–650° C. Under these conditions, the amount of residual methanol in the gas mixture leaving the catalyst is small, but the overall yield is reduced. Furthermore, the plant requires larger sized equipment, due to the high volume of gases that have to flow therethrough.

Generally, the concentration of the formaldehyde solution obtained ranges from 30 to 50 wt %. The processes describing the preparation of higher concentrations do it either by losing more methanol and formaldehyde in the gases, whereby the overall yield is lower, or by drawing two different currents off from the system, one concentrated and the other dilute.

An exception to dilution of the solution with water is described in the document FR 2 311 048 where the final scrubbing of the gases is effected with a relatively concentrated polymerized formaldehyde solution. In this case, no water is introduced into the system and solutions of a concentration ranging from 65 to 70% are obtained at the foot of the distillation column, without dilute side currents. Nevertheless, in spite of the advantage achieved by obtaining concentrated formaldehyde solutions directly from a manufacturing plant, the yield is, albeit slightly, adversely affected and the power consumption is increased.

For the great majority of applications for the preparation of glues and resins, it is sufficient to obtain a 55 wt % concentration of formaldehyde so as not to need to introduce any glue or resin distillation step. But, as said above, to achieve this concentration means having to scrub the non-condensable gases with little water, with the risk of losing a certain amount of methanol and, even, formaldehyde. One solution would be to scrub with very cold water, but this involves using cooling systems, which makes the process more expensive and does not make it profitable.

SUMMARY OF THE INVENTION

It is an object of the invention to overcome the above-mentioned problem. This object is achieved with a process of the type first mentioned above, which is characterized in that it uses a supply column and at least two additional heat exchangers associated with at least one absorption column; there taking place in the supply column an entry of air and an entry of methanol from the outside, as well as an entry of a first subcurrent of methanol, originating from an outgoing current of cold methanol from the foot of the supply column, the outgoing current recirculating successively through the additional heat exchangers and being divided into to the first subcurrent which returns to the head of the supply column and a second subcurrent flowing to said evaporator; there existing from the head of the supply column an outgoing current of a methanol and air mixture which flows between the supply column and the evaporator; and in that said cold methanol has been cooled, inside the supply column, by the evaporation of the methanol forming part of the methanol and air mixture.

According to a further aspect of the invention, in the additional heat exchanger situated upstream, the outgoing methanol current cools scrubbing water which subsequently attains the head of the absorption column, while in the heat exchangers situated downstream, the outgoing methanol current cools a solution for scrubbing the non-condensable gases which entrain methanol.

Preferably according to the invention, the additional heat exchangers are situated inside the absorption column.

According to a further feature of the invention, use is made in the evaporator of the heat released in the absorption steps to heat and evaporate the methanol-air mixture prior to reaction in the catalyst (preferably silver).

The invention contemplates that the fractional distillation (f) be performed at a pressure below atmospheric pressure.

Also according to the invention, use is made in a heat exchanger in communication with the catalyst of the heat produced in the catalyst during the catalytic reaction for the fractional distillation, with simultaneous cooling of the reaction mixture.

Preferably, the temperature of the catalyst ranges from 500° to 600° C. and the gases leaving the catalyst are cooled to 130° C. in said heat exchanger in communication with said catalyst.

According to a preferred aspect of the invention, the absorption takes place in said circulation step (c) in three stages at different temperatures in an aqueous methanol-and-formaldehyde-containing solution, such that in the first stage or at the foot, the temperature of the recirculating liquor ranges from 75° to 80° C.; in the second stage the temperature of the recirculating liquor ranges from 38° to 42° C. and in the third stage the temperature of the recirculating liquor ranges from 22° to 26° C.

Furthermore, it is contemplated that water at a temperature of 10° to 12° C. be used in step (e) where said non-condensable gases are cooled and scrubbed.

According to a further preferred aspect of the invention, part of the solution from the foot of the absorption column is supplied to the fractional distillation column at reduced pressure, preferably ranging from 40 to 46 kPa.

With the process, it becomes possible to cool the head of the absorption column without the need of any external cooling equipment. Advantage is taken of the fact that the heat required to evaporate the methanol on passing air therethrough comes from the mass of methanol itself which, therefore, is cooled. This is done in a column upstream of the evaporator as such.

The column is of the packed type and the fresh methanol plus the recirculated methanol is supplied to the head thereof and the air is supplied at the lower end. The cooled methanol is collected at the foot of the column. The amount of methanol collected at the foot of the column is successively caused to flow through the additional heat exchangers. All of them are fed through heat exchangers so as to take advantage of the temperature gradient achieved in the cooling. Basically there is achieved the cooling of the scrubbing currents recirculating in the absorption column as well as of the final gas scrubbing water. These heat exchangers are supplementary to the normal ones which use mains water for a first cooling. The heat exchangers may be external to the absorption column or may be situated within the column itself.

When preparing 55 wt % formaldehyde solutions, advantage may be had of this effect (i.e. the cooling obtained on evaporating the methanol by flowing air therethrough), by supply water cooled by this process to the head of the absorption column whereby both the methanol and the formaldehyde entrained by the non-condensable gases is retained much more effectively. When operating with this process, increases in the overall yield ranging from 0.4 to 0.8% (sum of that corresponding to the formaldehyde and to that of the methanol evaporated as formaldehyde) are achieved. If the enormous amounts of this product produced are taken into account, these yield increases mean considerable profits.

The heat exchange between the gases leaving the catalyst and the liquor at the foot of the distillation column may be direct or indirect. In the former case, the liquor from the foot of the column flows through the heat exchange tubes, with the gases flowing from the catalyst passing through the jacket. The heat exchange is sufficient to keep the column foot liquor boiling and to distill the methanol carried by the formaldehyde solution. Nevertheless, in this arrangement, the tubes end up by being fouled with formaldehyde polymers which reduce the heat exchange yield and even to the extent of obstructing the exchanger.

On the contrary, if the heat given up by the gases leaving the catalyst is used in a steam generator, there is obviously no fouling here and maximum use is made of the heat exchange. In turn, the steam generated here serves to distill the formaldehyde solution in the foot of the column, where there is no fouling either, since the steam flows through the tubes and not the formaldehyde solution. As a consequence of this latter arrangement, the heat performance of the process is also improved.

This process does not consume additional energy, since the methanol cooled prior to being supplied to the evaporator is heated by heat exchange with the absorption solutions which give off heat in the absorption. The heat contained in these solutions also allows the appropriate temperature to be maintained in the evaporator at all times. Thus the absorption solutions which must be cooled to maintain the appropriate temperatures for the absorption are cooled thanks to this heat exchange and thanks to the heat exchange with the cooled methanol temperatures are obtained at the head of the absorption column which are 10° to 15° C. lower than those obtained in the prior art processes. This process has the advantage that it is possible to operate as per document FR-2311048 for preparing concentrated formaldehyde solutions by cooling the scrubbing solution based on polymerized formol instead of water, improving the yield, since it becomes possible to reduce the methanol and formaldehyde content of the outflowing gases relative to the process described in said document.

BRIEF DESCRIPTION OF THE DRAWING

Two Figures are attached, FIG. 1 of which is a schematic view of the process of the invention

DESCRIPTION OF THE PREFERRED EMBODIMENT OF THE INVENTION

For a better understanding of the invention a number of examples are provided: Example 1, relating to the process of the invention (schematically illustrated in FIG. 1, as stated already above) and FIG. 2, relating to a conventional process, schematically illustrated in turn in FIG. 2. These examples describe continuous operation of the plant. The amounts given must be understood as when the plant has reached the steady state.

EXAMPLE 1

Figure 1:
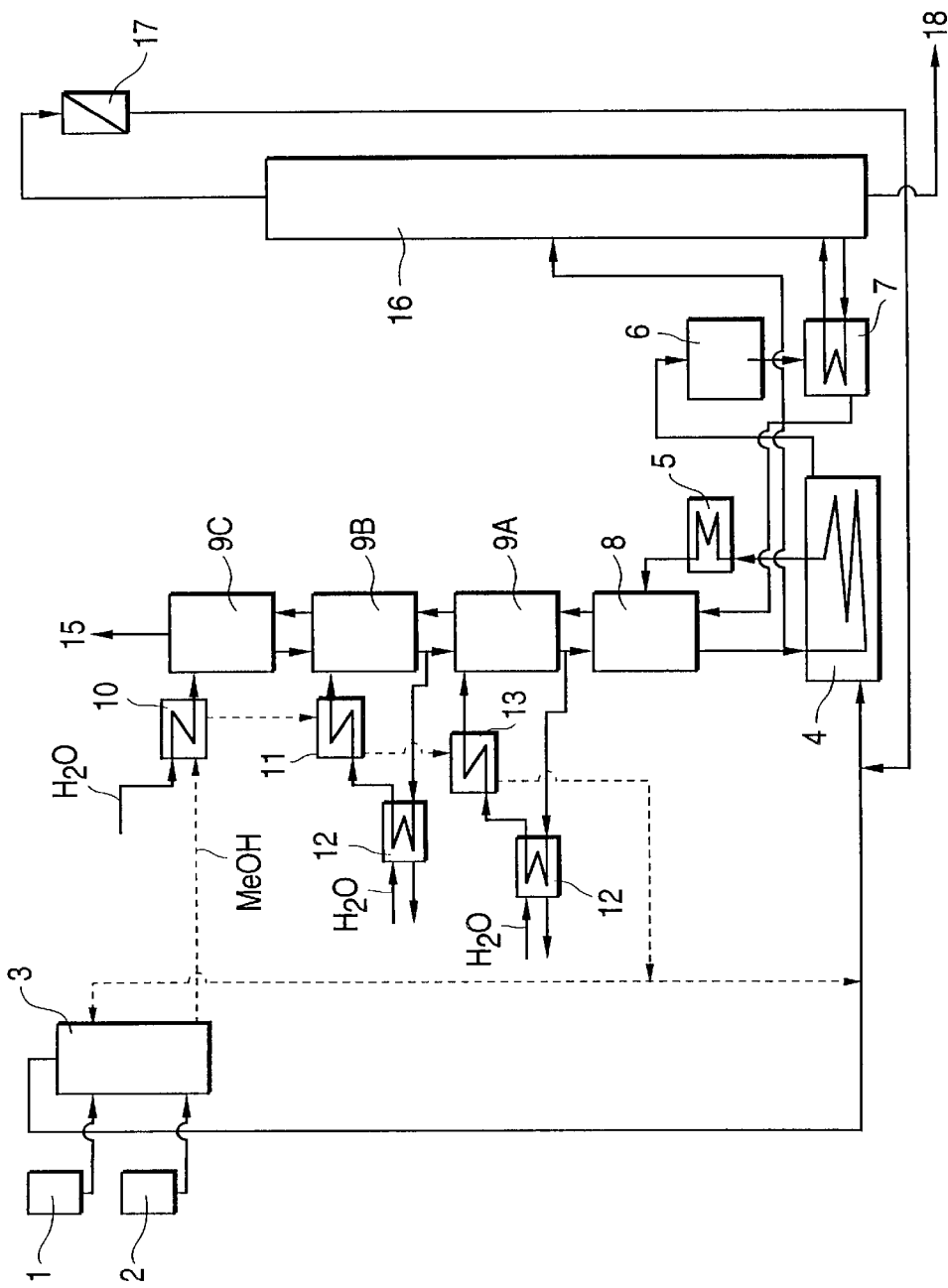

1,197 kg/h of methanol from tank 1 and 2,260 kg/h of air supplied with the aid of a blower 2 are supplied respectively to the head of the supply column 3 and to the foot of said column, in a plant in accordance with FIG. 1. The methanol cooled by the partial evaporation thereof cools the methanol flowing from the tank and the methanol recirculating through the supply column.

2,260 kg/h of air, containing 179.4 kg/h of methanol, exit from the head of the column 3. This mixture is supplied to the evaporator 4.

The methanol M collected at the foot of the supply column 3, 5,577 kg/h, at a temperature of 8° C., is successively caused to flow through the additional heat exchangers 10, 11 and 13. Water ($H_2O$) flows in countercurrent in the upstream additional heat exchanger 10, is cooled and is supplied to the head of column 9. An absorbent solution flows in countercurrent in the downstream additional heat exchangers 11 and 13. A current of water A also flows through these heat exchangers. At the exit from the additional heat exchanger 13, located downstream, the current of methanol, at a temperature of 25° C., is divided into two subcurrents: a first subcurrent formed by 4,576.4 kg/h, which is recirculated to the supply column 3 and a second subcurrent of 1,000.6 kg/h, which is fed to the evaporator 4. These additional heat exchangers may be located in the interior of the column 9.

The evaporator 4 is also supplied with 770 kg/h of methanol recovered from the distillation column 16 and condensed in the condenser 17. 1,967 kg/h of methanol are evaporated in the evaporator 4 at a temperature of 50.5° C., thanks to the heat supplied in the first absorption stage 8, by the liquor flowing from the column 8 to the evaporator 4, intermediate heat exchanger 5 and column 8 again. This liquor is the absorption solution of the gases leaving the catalyst 6, formed by water, methanol and formaldehyde.

The methanol-air mixture thus passes to the silver catalyst 6 which is held at a temperature of 560° C. such that it converts 1,185 kg/h of methanol into formaldehyde. The gases flowing from the catalyst contain 1,000 kg/h of formaldehyde, 782.2 kg/h of methanol and 470 kg/h of water, apart from the non-condensable gases formed by hydrogen produced in the reaction (21.8 vol %), small amounts of carbon dioxide (3.7 vol %), carbon monoxide (less than 0.1 vol %), methane (less than 0.1 vol %), traces of oxygen (less than 0.1 vol %), with the air nitrogen being the rest.

These gases (i.e., both the condensable gases and the non-condensable gases, plus the water vapour formed) are cooled in the heat exchanger 7 (which is in communication with the catalyst 6), with the liquor from the foot of the distillation column 16 to a temperature of 140° C.; this liquor is a 55% solution of formaldehyde, with less than 1% of methanol.

The now cooled gases mentioned in the foregoing paragraph flow from the heat exchanger 7 to the absorption column 8 where they are scrubbed with an absorbent solution formed by water, methanol and formaldehyde and a solution temperature of 78° to 80° C. is held with the aid of the heat exchanger 5, after exchanging part of its heat content in the evaporator, with a view to maintaining the evaporator at an appropriate temperature for the evaporation of the air-methanol mixture.

The gases exiting from the column 8 (i.e. the permanent gases which do not dissolve, plus the soluble gases which have not yet been dissolved) flow to the column 9 where thanks to the heat exchanger 14 (through which water flows as cooling liquor) and the additional heat exchanger 13 (located downstream and through which cold methanol flows as cooling liquor), a recirculation of 12 m$^3$/h of the absorbent solution (i.e., water, methanol and formaldehyde) is maintained at a temperature of 40° C. This recirculation takes place between the foot and the head of column 9A.

A flow of 1.2 m$^3$/h is withdrawn from the column 9B just above the point where the recirculation from column 9A enters, and is recirculated after being cooled to 25° C. by the heat exchanger 12 (through which water flows as cooling liquor) and the additional heat exchanger 11 (immediately following the additional heat exchanger 10 situated upstream and through which cold methanol flows as cooling liquor). This current is an absorbent solution, as stated above, although with a lower methanol and formaldehyde concentration. This current recirculates between the foot and the head of column 9B.

Finally, 336 kg/h of water cooled to 12° C. are added at the head of column 9C, whereby the non-condensable gases exiting from the column 9 and flowing to the burner 15 contain 0.4 g/m$^3$ of formaldehyde and 1.25 g/m$^3$ of methanol. These amounts represent a loss of yield, calculated as formaldehyde, of 0.27%.

2,585 kg/h of the liquor recirculating in stage 8 are supplied to the distillation column 16 to remove the methanol as distillate (770 kg/h). This methanol, after condensation in the condenser 17 returns to the evaporator 4. 1,815 kg/h of solution containing 55 wt % of formaldehyde and less than 1 wt % of methanol are recovered from the foot of column 16.

EXAMPLE 2

Figure 2:
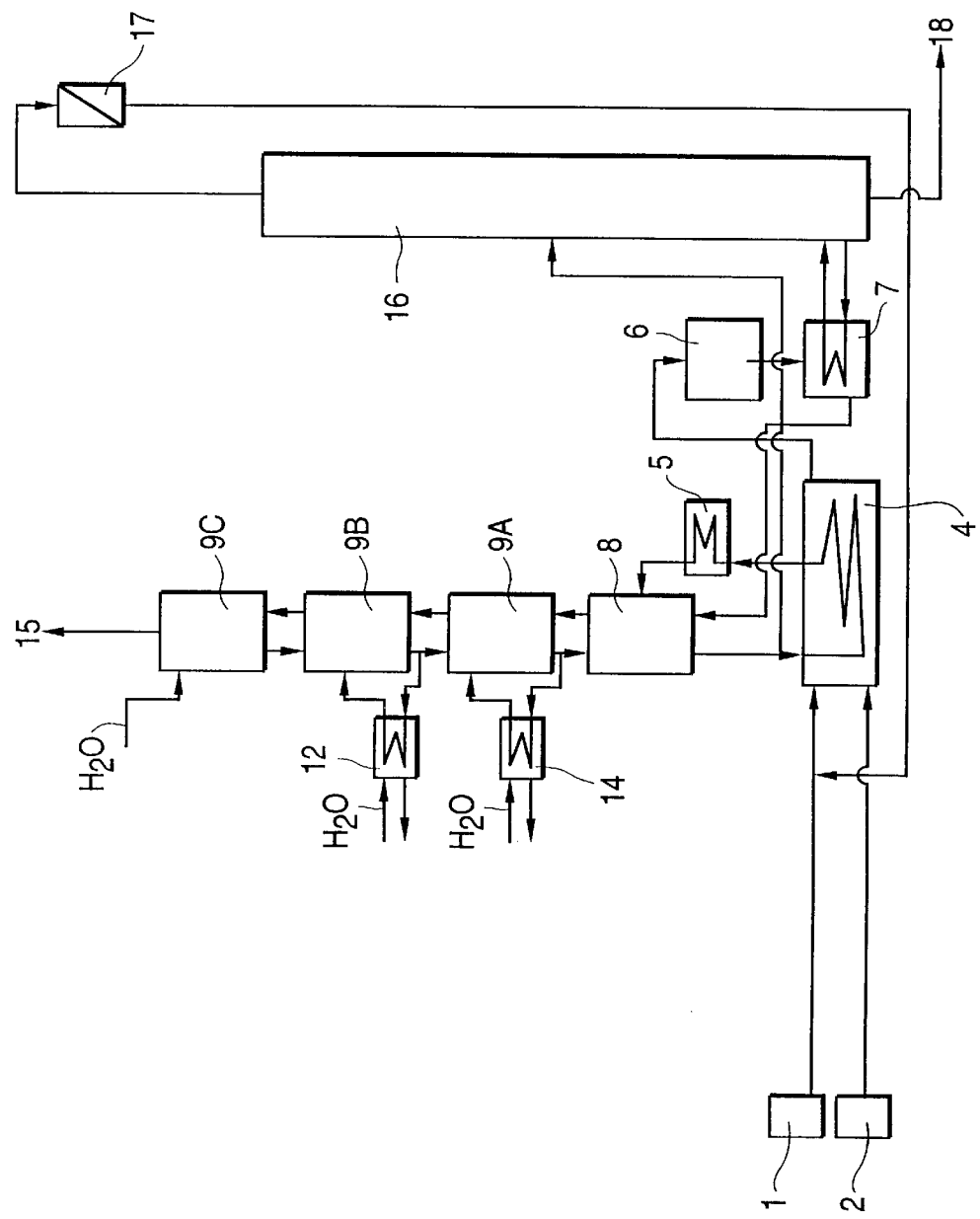
FIG. 2 is a schematic view of a conventional process.

In the plant of FIG. 2, 997.3 kg/h of methanol from the tank 1 and 1,869 kg/h of air with the aid of the blower 2 are supplied to the evaporator 4. Methanol recovered from the distillation column 16 is also fed to the evaporator 4. 1,629.3 kg/h of methanol are evaporated in the evaporator 4 thanks to the heat provided by the column 8, during the absorption stage occurring therein. The methanol-air mixture flows to the silver catalyst 6 which is held at 560° C. such that 980 kg/h of methanol are converted to formaldehyde. The gases exiting from the catalyst contain 839.5 kg/h of formaldehyde, 649.5 kg/h methanol and 390 kg/h of water, plus the non-condensable gases formed by hydrogen produced in the reaction (22 vol %), small amounts of carbon dioxide (4.1 vol %), carbon monoxide (less than 0.1 vol %), methane (less than 0.1 vol %), traces of oxygen (less than 0.1 vol %), with the air nitrogen being the rest.

These gases are cooled, condensed and scrubbed as described in Example 1 with the difference that the coolings with cold methanol have been suppressed and cooled water is not fed through the head of the column, but 289 kg/h of water at room temperature (25° C.). Thus, the temperature at the head of this column reaches 30° C. The outflowing gases which are fed to the burner 15 contain 0.8 g/m$^3$ of formaldehyde and 5 g/m$^3$ of methanol. These amounts represent a loss of yield calculated as formaldehyde of 0.97%.

2,150.6 kg/h of the liquor recirculating in 8 are supplied to the column 16 where 632 kg/h of methanol are distilled and returned to the evaporator. 1,518 kg/h of a solution containing 54.6% of formaldehyde and less than 1% of methanol are recovered from the foot of the column.

It will be seen that the increase in formaldehyde yield as a result of the scrubbing with cold solutions reaches 0.70% in this representative example.

What I claim is:

1. A process for the continuous preparation of aqueous formaldehyde solutions, the process comprising the following steps:

(a) supplying air and methanol to an evaporator, in which the methanol is evaporated, forming a gas phase mixture of methanol and air;

(b) reacting said gas phase mixture of methanol and air over a catalyst at an elevated temperature, to obtain a reaction mixture comprising formaldehyde resulting from the partial conversion of methanol, as well as water vapour and non-condensable gases;

(c) flowing said reaction mixture through an absorption column where said mixture is absorbed in an aqueous solution flowing in the opposite direction;

(d) separating said aqueous solution and said non-condensable gases in said absorption column;

(e) cooling and scrubbing said non-condensable gases which entrain small amounts of methanol and formaldehyde; and (f) fractionally distilling said aqueous solution, with a corresponding separation of the methanol, wherein there is used a supply column and at least two additional heat exchangers associated with said absorption column;

there taking place in said supply column an entry of air and an entry of methanol from the outside, as well as an entry of a first refrigeration subcurrent of refrigerating methanol, originating from an outgoing current of cold refrigerating methanol from the foot of the supply column;

said outgoing current recirculating successively through said additional heat exchangers and being divided into said first refrigeration subcurrent which returns to the head of the supply column and a second subcurrent flowing to said evaporator;

there existing from the head of the supply column an outgoing current of a methanol and air mixture which flows between said supply column and said evaporator;

and wherein said cold methanol has been cooled, inside said supply column, by the evaporation of the methanol forming part of said methanol and air mixture.

2. The process of claim 1, wherein in the additional heat exchanger situated upstream, said outgoing methanol current cools scrubbing water which subsequently attains the head of said absorption column.

3. The process of claim 2, wherein in the heat exchangers situated downstream, said outgoing methanol current cools a solution for scrubbing the non-condensable gases which entrain methanol.

4. The process of claim 1, wherein said additional heat exchangers are situated inside the absorption column.

5. The process of claim 1, wherein use is made in said evaporator of the heat released in the absorption steps to heat and evaporate the methanol-air mixture prior to reaction in the catalyst.

6. The process of claim 1, wherein said fractional distillation is performed at a pressure below atmospheric pressure.

7. The process of claim 1, wherein use is made in a heat exchanger in communication with said catalyst of the heat produced in the catalyst during the catalytic reaction for said fractional distillation, with simultaneous cooling of said reaction mixture.

8. The process of claim 1, wherein said catalyst is silver.

9. The process of claim 1, wherein the temperature of the catalyst ranges from 500° to 600° C.

10. The process of claim 7, wherein the gases leaving said catalyst are cooled to 130° C. in said heat exchanger in communication with said catalyst.

11. The process of claim 1, wherein the absorption takes place in said step (c) in three stages at different temperatures in an aqueous methanol-and-formaldehyde-containing solution.

12. The process of claim 11, wherein in the first stage or at the foot, the temperature of said aqueous solution flowing in the opposite direction ranges from 75° to 80° C.

13. The process of claim 11, wherein in the second stage the temperature of said aqueous solution flowing in the opposite direction ranges from 38° to 42° C.

14. The process of claim 11, wherein in the third stage the temperature of said aqueous solution flowing in the opposite direction ranges from 22° to 26° C.

15. The process of claim 1, wherein water at a temperature of 10° to 12° C. is used in said step (e) where said non-condensable gases are cooled and scrubbed.

16. The process of claim 1, wherein part of the solution from the foot of the absorption column is supplied to the fractional distillation column at reduced pressure.

17. The process of claim 16, wherein said pressure ranges from 40 to 46 kpa.

18. The process of claim 1, wherein the aqueous formaldehyde solution has a concentration ranging from 53 wt % to 57 wt %.

* * * * *